(12) United States Patent
Heim et al.

(10) Patent No.: US 6,533,781 B2
(45) Date of Patent: Mar. 18, 2003

(54) ELECTROSURGICAL INSTRUMENT

(75) Inventors: Warren Paul Heim, Boulder, CO (US); Michael Olichney, Boulder, CO (US); James L. Brassell, Boulder, CO (US)

(73) Assignee: Team Medical LLC, Boulder, CO (US)

( * ) Notice: Subject to any disclaimer, the term of this patent is extended or adjusted under 35 U.S.C. 154(b) by 81 days.

(21) Appl. No.: 09/751,223

(22) Filed: Dec. 29, 2000

(65) Prior Publication Data

US 2001/0012936 A1 Aug. 9, 2001

Related U.S. Application Data

(63) Continuation-in-part of application No. 08/997,365, filed on Dec. 23, 1997.

(51) Int. Cl.$^7$ .............................................. A61B 18/14
(52) U.S. Cl. ......................................... 606/45; 606/49
(58) Field of Search .............................. 606/41, 45, 49

(56) References Cited

U.S. PATENT DOCUMENTS

| | | | |
|---|---|---|---|
| 874,178 A | 12/1907 | DeForest | |
| 1,713,970 A | 6/1929 | Lowry et al. | |
| 1,814,791 A | 7/1931 | Ende | |
| 3,799,168 A | 3/1974 | Peters | 128/303.14 |
| 3,987,795 A | 10/1976 | Morrison | 128/303.14 |
| 4,043,342 A | 8/1977 | Morrison, Jr. | 128/303.14 |
| 4,074,718 A | 2/1978 | Morrison, Jr. | 128/303.45 |
| 4,161,950 A | 7/1979 | Doss et al. | 128/303.14 |
| 4,202,337 A | 5/1980 | Hren et al. | 128/303.14 |
| 4,228,800 A | 10/1980 | Degler, Jr. et al. | 128/303.14 |
| 4,248,231 A | 2/1981 | Herczog et al. | 128/303.14 |
| 4,314,559 A | 2/1982 | Allen | 128/303.14 |
| 4,333,467 A | 6/1982 | Domicone | 128/303.14 |
| 4,449,926 A | 5/1984 | Weiss | 433/32 |
| 4,481,057 A | 11/1984 | Beard | 156/216 |
| 4,492,231 A | 1/1985 | Auth | 128/303.17 |
| 4,534,347 A | 8/1985 | Taylor | 128/303.1 |
| 4,545,375 A | 10/1985 | Cline | 128/303.14 |
| 4,565,200 A | 1/1986 | Cosman | 128/642 |

(List continued on next page.)

FOREIGN PATENT DOCUMENTS

WO  WO 96/34571  11/1996  ........... A61B/17/39

*Primary Examiner*—Lee Cohen
(74) *Attorney, Agent, or Firm*—Marsh Fischmann & Breyfoggle LLP

(57) ABSTRACT

An improved electrosurgical instrument and method is disclosed for reducing smoke generation at a surgical site. The electrosurgical instrument comprises a metal body having an outer insulating layer to reduce thermal/electrical discharge from non-functional portions of the instrument. In one aspect of the invention, an insulating layer having a thermal conductance of about 1.2 W/cm$^{2°}$ K and a dielectric withstand strength of at least about 50 volts is employed. Such insulating layer may advantageously comprise silicon and/or carbon. In another aspect of the invention, the metal body is provided to have a thermal conductivity of at least about 0.35 W/cm° K, and may advantageously comprise a metal selected from the group: gold, silver, aluminum, copper tantalum, tungsten, columbium and molybdenum. In yet a further aspect, the metal body may include an intermediate layer that defines a peripheral edge portion of reduced cross-section (e.g., about 0.001 inches thick or less) for electrosurgical signal transmission. Such intermediate layer may comprise a metal having a melting point of at least about 2600° F. Heat sink means may be included in various embodiments to establish a thermal gradient away from functional portions of the instrument (i.e., by removing heat from the metal body). In one embodiment, the heat sink means may comprise a phase change material that changes from a first phase to a second phase upon absorption of thermal energy from the metal body.

38 Claims, 5 Drawing Sheets

U.S. PATENT DOCUMENTS

| | | | |
|---|---|---|---|
| 4,589,411 A | 5/1986 | Friedman | 128/303.14 |
| 4,622,966 A | 11/1986 | Beard | 128/303.14 |
| 4,657,016 A | 4/1987 | Garito et al. | 128/303.13 |
| 4,785,807 A | 11/1988 | Blanch | 128/303.14 |
| 4,793,346 A | 12/1988 | Mindich | 128/305 |
| 4,823,791 A | 4/1989 | D'Amelio et al. | 123/303.14 |
| 4,848,337 A | 7/1989 | Shaw et al. | 128/303.1 |
| 4,927,420 A * | 5/1990 | Newkirk et al. | 606/45 |
| 4,931,047 A | 6/1990 | Broadwin et al. | 604/22 |
| 4,976,711 A | 12/1990 | Parins et al. | 606/48 |
| 5,015,227 A | 5/1991 | Broadwin et al. | 604/22 |
| 5,030,218 A * | 7/1991 | Alexander | 606/45 |
| 5,080,660 A | 1/1992 | Buelna | 606/45 |
| 5,160,334 A | 11/1992 | Billings et al. | 606/34 |
| 5,167,659 A | 12/1992 | Ohtomo et al. | 606/40 |
| 5,267,994 A | 12/1993 | Gentelia et al. | 606/15 |
| 5,308,311 A | 5/1994 | Eggers et al. | 606/28 |
| 5,318,562 A | 6/1994 | Levy et al. | 606/16 |
| 5,380,320 A | 1/1995 | Morris | 606/33 |
| 5,382,247 A | 1/1995 | Cimino et al. | 606/45 |
| 5,464,390 A | 11/1995 | Arnett et al. | 604/35 |
| 5,520,684 A | 5/1996 | Imran | 606/41 |
| 5,549,604 A | 8/1996 | Sutcu et al. | 606/45 |
| 5,554,172 A | 9/1996 | Horner et al. | 607/88 |
| 5,643,256 A | 7/1997 | Urueta | 606/45 |
| 5,693,060 A | 12/1997 | Speiser | 606/45 |
| 5,697,926 A | 12/1997 | Weaver | 606/41 |
| 5,702,387 A | 12/1997 | Arts et al. | 606/45 |
| 5,713,895 A | 2/1998 | Lontine et al. | 606/49 |
| 6,030,381 A * | 2/2000 | Jones et al. | 606/45 |
| 6,039,735 A | 3/2000 | Greep | 606/45 |
| 6,059,783 A | 5/2000 | Kirwan, Jr. | 606/51 |
| 6,066,137 A | 5/2000 | Greep | 606/45 |
| 6,126,656 A * | 10/2000 | Billings | 606/45 |
| 6,132,427 A * | 10/2000 | Jones et al. | 606/45 |

* cited by examiner

ELECTROSURGICAL INSTRUMENT

RELATED APPLICATIONS

This patent application is a continuation-in-part of a U.S. patent application entitled "IMPROVED ELECTROSURGICAL INSTRUMENT", having Ser. No. 08/997,365, filed on Dec. 23, 1997, the entirety of which is hereby incorporated by reference.

FIELD OF THE INVENTION

The present invention relates to surgical methods and apparatus for applying an electrosurgical signal to a tissue site to achieve a predetermined surgical effect, and more particularly, to an improved electrosurgical instrument and method to achieve such effect with reduced attendant smoke generation at the surgical site.

BACKGROUND OF THE INVENTION

The potential applications and recognized advantages of employing electrical energy in surgical procedures continue to increase. In particular, for example, electrosurgical techniques are now being widely employed to provide significant localized surgical advantages in both open and laparoscopic applications, relative to traditional surgical approaches.

Electrosurgical techniques typically entail the use of a hand-held instrument, or pencil, that transfers radio frequency (RF) electrical energy to a tissue site, a source of radio frequency (RF) electrical energy, and an electrical return path device, commonly in the form of a return electrode pad positioned under a patient (i.e. a monopolar system configuration) or a smaller return electrode positionable in bodily contact at or immediately adjacent to the surgical site (i.e. a bipolar system configuration). The waveforms produced by the RF source yield a predetermined electrosurgical effect, namely tissue cutting or coagulation.

Despite numerous advances in the field, currently-employed electrosurgical techniques often generate substantial smoke at the surgical site. Such smoke occurs as a result of tissue heating and the associated release of hot gases/vapor from the tissue site (e.g., in the form of an upward plume). As will be appreciated, any generation of smoke may impede observation of the surgical site during surgical procedures. Additionally, the generation of smoke results in attendant fouling of the atmosphere in the surgical theater. Clearly, these environmental impacts may adversely detract from the performance of medical personnel. Further, there is growing concern that the smoke may be a medium for the transport of pathogens away from the surgical site, including viruses such as HIV. Such concerns have contributed to the use of face shields and masks by surgical personnel.

To date, implemented approaches to deal with smoke have focused on the use of devices that either evacuate the smoke by sucking the same into a filtering system, or that merely blow the smoke away from the surgical site by a pressurized gas stream. Smoke evacuators typically require the movement of large amounts of air to be effective. As such, evacuators tend to be not only noisy but also space consuming. Approaches for blowing smoke away from the surgical site fail to address many of the above-noted concerns, since smoke is not actually removed from the surgical environment. Moreover, both of the above-noted approaches entail the use of added componentry, thereby increasing the cost and complexity of electrosurgical systems.

SUMMARY OF THE INVENTION

Accordingly, a primary objective of the present invention is to provide an apparatus and method for use in electrosurgery that results in reduced generation of smoke at a surgical site.

Another objective of the present invention is to provide an apparatus and method for use in electrosurgery that yields less eschar accumulation on the electrosurgical instrument utilized.

An additional objective of the present invention is to provide an apparatus and method for use in electrosurgery that provides for reduced charring along an electrosurgical incision.

Yet another objective is to realize one or more of the foregoing objectives in a manner which does not significantly impact space or cost requirements, and which maintains and potentially enhances the effectiveness of electrosurgical procedures.

In addressing these objectives, the present inventors have recognized that a large portion of the smoke generated utilizing known electrosurgical instruments results from the transmission of electrosurgical energy to tissue from areas of known electrosurgical instruments that are actually intended to be "non-functional" for purposes of achieving the desired electrosurgical effect (i.e. cutting or coagulation). That is, while known electrosurgical instruments include "functional" portions which are designed to be selectively positioned to direct an electrosurgical signal to an intended surgical location (e.g. along a desired incision line), the discharge of energy is not effectively restricted to the functional portions.

More generally in this regard, energy discharge from electrosurgical instruments may be in the form of electrical energy and/or thermal energy. Electrical energy is transferred whenever the electrical resistance of a region between an electrosurgical instrument and tissue can be broken down by the voltage of the electrosurgical signal. Thermal energy is transferred when thermal energy that has accumulated in the electrosurgical instrument overcomes the thermal resistance between the instrument and the tissue (i.e. due to temperature differences therebetween).

The discharge of electrical and thermal energy from nonfunctional areas of known electrosurgical instruments results in unnecessary heating of tissue at a tissue site. In the case of electrical energy discharge, thermal energy is generated as a result of tissue resistance. As the amount of thermal energy at a tissue site increases, the electrical resistance at the surgical site also increases, thereby resulting in the further generation of heat. Such increased heating may in turn result in tissue charring as well as the splattering of tissue matter onto the electrosurgical instrument employed. The splattered tissue matter may accumulate as eschar on the electrosurgical instrument and present a further resistance/heat source to the surgical site. Eschar accumulation on electrosurgical instruments also raises the need for medical personnel to periodically suspend a procedure in order to clean the eschar from the electrosurgical instrument. As can be appreciated, such disturbances can adversely impact an electrosurgical procedure.

In short, the present inventors have recognized that any undesired and unnecessary discharge of electrosurgical energy from non-functional portions of an electrosurgical instrument to a surgical site can have a negative and cascading effect of unnecessary heat generation and resultant smoke generation, eschar build-up on the electrosurgical instrument and unnecessary tissue charring. In the later regard, it is believed that tissue charring may adversely affect healing.

In conjunction with the above-referenced recognition, the present invention provides an apparatus and method for reducing unnecessary/undesired electrical and/or thermal discharge during electrosurgical procedures. Such reduction(s) are achieved via enhanced localization of electrical and thermal energy transmission to a tissue site. More particularly, the present invention markedly reduces electrical/thermal discharge from non-functional areas of an electrosurgical instrument by insulating the nonfunctional areas and/or by providing for an effective level of heat removal away from functional portions of an electrosurgical instrument and/or by otherwise enhancing the localized delivery of an electrosurgical signal to a tissue site.

In this regard, the present invention comprises an electrosurgical instrument that includes a metal body for carrying an electrosurgical signal and an outer insulating layer positioned over at least a portion of the metal body (i.e., a non-functional portion). The metal body includes a main body portion and a peripheral edge portion, the peripheral edge portion being functional for the conveyance of the electrosurgical signal to a tissue site.

In one aspect of the present invention, the outer insulating layer may be advantageously provided to have a maximum thermal conductance of about 1.2 W/cm$^2$-° K when measured at about 300° K, more preferably about 0.12 W/cm$^2$-° K or less when measured at about 300° K, and most preferably about 0.03 W/cm$^2$-° K when measured at about 300° K. For purposes hereof, thermal conductance is intended to be a measure of the overall thermal transfer across any given cross section (e.g. of the insulation layer), taking into account both the thermal conductivity of the materials comprising such layer and the thickness of the layer (i.e. thermal conductance of layer=thermal conductivity of material comprising the layer (W/cm° K)/thickness of the layer (cm)). In relation to the foregoing aspect, the insulation layer should also exhibit a dielectric withstand voltage of at least the peak-to-peak voltages that may be experienced by the electrosurgical instrument during surgical procedures. The peak voltages will depend upon the settings of the RF source employed, as may be selected by clinicians for particular surgical procedures. For purposes of the present invention, the insulation layer should exhibit a dielectric withstand voltage of at least about 50 volts, and more preferably, at least about 150 volts. As employed herein, the term dielectric withstand voltage means the capability to avoid an electrical breakdown (e.g. an electrical discharge through the insulating layer).

In one embodiment, the outer insulating layer advantageously comprises a polymeric compound. More particularly, such polymeric compound includes at least about 10% (by weight), and most preferably at least about 20% (by weight), of a component selected from a group comprising: silicon and carbon. In this regard, silicon-based, polymeric insulating layers have been found to be of particular benefit. Such silicon-based, polymeric layers have a thermal conductivity of about 0.003 W/cm° K or less when measured at about 300° K. Such silicon-based, polymeric layers have been found to be effective when having a thickness of about 0.25 mm or more. Further, such silicon-based, polymeric layers have a dielectric strength of at least about 12 Kv/mm. In a related embodiment, the insulation layer may comprise polytetrafluoroethylene.

In another embodiment, the insulating layer may comprise a ceramic material (e.g., applied to the metal body via dipping, spraying, etc, then cured via drying, firing, etc.). Preferably, the ceramic insulating layer should be able to withstand temperatures of at least about 2000° F. The ceramic insulating layer may comprise various metal/non-metal combinations, including for example compositions that comprise the following: aluminum oxides (e.g. alumina and $Al_2O_3$), zirconium oxides (e.g. $Zr_2O_3$), zirconium nitrides (e.g. ZrN), zirconium carbides (e.g. ZrC), boron carbides (e.g. $B_4C$), silicon oxides (e.g. $SiO_2$), mica, magnesium-zirconium oxides (e.g. $(Mg—Zr)O_3$), zirconium-silicon oxides (e.g. $(Zr—Si)O_2$), titanium oxides (e.g., $TiO_2$) tantalum oxides (e.g. $Ta_2O_5$), tantalum nitrides (e.g. TaN), tantalum carbides (e.g., TaC), silicon nitrides (e.g. $Si_3N_4$), silicon carbides (e.g. SiC), tungsten carbides (e.g. WC) titanium nitrides (e.g. TiN), titanium carbides (e.g., TiC), nibobium nitrides (e.g. NbN), niobium carbides (e.g. NbC), vanadium nitrides (e.g. VN), vanadium carbides (e.g. VC), and hydroxyapatite (e.g. substances containing compounds such as $3Ca_3(PO_4)_2Ca(OH)_2$ $Ca10(PO_4)_6(OH)_2$ $Ca5(OH)(PO_4)_3$, and $Ca_{10}H_2O_{26}P_6$). One or more ceramic layers may be employed, wherein one or more layers may be porous, such as holes filled with one or more gases or vapors. Such porous compositions will usually have lower thermal conductivity than the nonporous materials. An example of such materials are foam e.g., an open cell silicon carbide foam.

As may be appreciated, in other embodiments the insulating layer may be defined by at least one inner layer (e.g. adjacent to the metal body) that includes a ceramic material, and at least one outer layer that comprises a polymeric compound as noted above. Such inner and outer layers may be advantageously employed to yield an average maximum thermal conductivity of about 0.006 W/cm-° K or less where measured at 300° K. The inner layer and outer layer may preferably each have a thickness of between about 0.001 and 0.2 inches, and most preferably between about 0.005 and 0.100 inches.

In another aspect of the present invention, the metal body of the inventive electrosurgical instrument may be provided to have a thermal conductivity of at least about 0.35 W/cm° K when measured at about 300° K. By way of primary example, the metal body may advantageously comprise at least one metal selected from a group comprising: silver, copper, aluminum, gold, tungsten, tantalum, columbium (i.e., niobium), and molybdenum. Alloys comprising at least about 50% (by weight) of such metals may be employed, and even more preferably at least about 90% (by weight). Additional metals that may be employed in such alloys include zinc.

In yet another aspect of the present invention, at least a portion of the peripheral edge portion of the metal body is not insulated (i.e. not covered by the outer insulating layer). In connection therewith, when the outer peripheral edge portion comprises copper such portion may be coated (e.g. about 10 microns or less) with a biocompatible metal. By way of example, such biocompatible metal may be selected from the group comprising: nickel, silver, gold, chrome, titanium tungsten, tantalum, columbium (i.e., niobium), and molybdenum.

In an additional aspect of the invention, it has also been determined that a laterally tapered, or sharpened, uninsulated peripheral edge portion having a maximum cross-sectional thickness which is about 1/10 of the maximum cross-sectional thickness of the main body portion is particularly effective for achieving localized electrosurgical signal delivery to a tissue site. In the later regard, it has also been determined preferable that the outer extreme of the peripheral edge portion of the metal body have a thickness of about 0.001 inches or less.

In an additional related aspect of the present invention, the metal body may comprise two or more layers of different materials. More particularly, at least a first metal layer may be provided to define an exposed peripheral edge portion of the metal body that is functional to convey an electrosurgical signal to tissue as described above. Preferably, such first metal layer may comprise a metal having a melting temperature greater than about 2600° F., more preferably greater than about 3000° F., and even more preferably greater than about 4000° F., thereby enhancing the maintenance of a desired peripheral edge thickness during use (e.g. the outer extreme edge noted above). Further, the first metal layer may preferably have a thermal conductivity of at least about 0.35 W/cm° K when measured at 300° K.

For living human/animal applications, the first metal layer may comprise a first material selected from a group consisting of tungsten, tantalum, columbium (i.e., niobium), and molybdenum. All of these metals have thermal conductivities within the range of about 0.5 to 1.65 W/cm° K when measured at 300° K. Preferably, alloys comprising at least about 50% by weight of at least one of the noted first materials may be employed, and even more preferably at least about 90% by weight.

In addition to the first metal layer the metal body may further comprise at least one second metal layer on the top and/or bottom of the first metal layer. Preferably, a first metal layer as noted above is provided in a laminate arrangement between top and bottom second metal layers. To provide for rapid heat removal, the second metal layer(s) preferably has a thermal conductivity of at least about 2 W/cm° K. By way of primary example, the second layer(s) may advantageously comprise a second material selected from a group consisting of copper, gold, silver and aluminum. Preferably, alloys comprising at least about 50% of such materials may be employed, and even more preferably at least about 90% by weight. It is also preferable that the thickness of the first metal layer and of each second metal layer (e.g. for each of a top and bottom layer) be defined at between about 0.001 and 0.25 inches, and even more preferably between about 0.005 and 0.1 inches.

As may be appreciated, multi-layered metal bodies of the type described above may be formed using a variety of methods. By way of example, sheets of the first and second materials may be role-bonded together then cut to size. Further, processes that employ heat or combinations of heat and pressure may also be utilized to yield a laminated metal body.

In a further aspect of the present invention, the inventive electrosurgical instrument may further comprise a heat sink for removing thermal energy from the metal body. In this regard, the provision of a heat sink establishes a thermal gradient away from the peripheral edge of the metal body, thereby reducing undesired thermal transfer to a tissue site. More particularly, it is preferable for the heat sink to operate so as to maintain the maximum temperature on the outside surface of the insulating layer at about 160° C. or less, more preferably at about 80° C. or less, and most preferably at 60° C. or less. Relatedly, it is preferable for the heat sink to operate to maintain an average metal body temperature of about 500° C. or less, more preferably of about 200° C. or less, and most preferable of about 100° C. or less.

In one approach, the heat sink may comprise a vessel comprising a phase change material that either directly contacts a portion of the metal body (e.g. a support shaft portion) or that contacts a metal interface provided on the vessel which is in turn in direct contact with a portion of the metal body (e.g. a support shaft portion). Such phase change material changes from a first phase to a second phase upon absorption of thermal energy from the metal body. In this regard, the phase change temperature for the material selected should preferably be greater than the room temperature at the operating environment and sufficiently great as to not change other than as a consequence of thermal heating of the electrosurgical instrument during use. Such phase change temperature should preferably be greater than about 30° C. and most preferably at least about 40° C. Further, the phase change temperature should be less than about 225° C. Most preferably, the phase change temperature should be less than about 85° C.

The phase change may be either from solid to liquid (i.e., the phase change is melting) or from liquid to vapor (i.e., the phase change is vaporization) or from solid to vapor (i.e., the phase change is sublimation). The most practical phase changes to employ are melting and vaporization. By way of example, such phase change material may comprise a material that is an organic substance (e.g., fatty acids such as stearic acid, hydrocarbons such as paraffins) or an inorganic substance (e.g., water and water compounds containing sodium, such as, sodium silicate (2-)-5-water, sodium sulfate-10-water).

In another approach, the heat sink may comprise a gas flow stream that passes in direct contact with at least a portion of the metal body. Such portion may be a peripheral edge portion and/or a shaft portion of the metal body that is designed for supportive interface with a holder for hand-held use. Alternatively, such portion may be interior to at least a portion of the metal body, such as interior to the exposed peripheral edge portion and/or the shaft portion of the metal body that is designed for supportive interface with a holder for hand-held use. In yet other approaches, the heat sink may simply comprise a thermal mass (e.g. disposed in a holder).

In one arrangement of the present invention, an electrosurgical instrument comprises a main body portion having a blade-like configuration at a first end and an integral, cylindrical shaft at a second end. The main body may comprise a highly-conductive metal and/or multiple metal layers as noted. At least a portion of the flattened blade end of the main body is coated with a ceramic-based and/or silicon-based, polymer insulating layer, except for the peripheral edge portion thereof. The cylindrical shaft of the main body is designed to fit within an outer holder that is adapted for hand-held use by medical personnel. Such holder may also include a chamber comprising a phase-change material or other heat sink as noted hereinabove. Additionally, electrical, push-button controls may be incorporated into the holder for selectively controlling the application of one or more, predetermined, electrosurgical signal(s) from an RF energy source to the flattened blade via the shaft of the main body portion.

In the latter regard, conventional electrosurgical signals may be advantageously employed in combination with one or more of the above-noted electrosurgical instrument features. In particular, the inventive electrosurgical instrument yields particular benefits when employed with electrosurgical signals and associated apparatus of the type described in U.S. Pat. No. 6,074,387, hereby incorporated by reference in its entirety.

Numerous modifications and additions to the present invention will be apparent to those skilled in the art upon consideration of the further description that follows.

DETAILED DESCRIPTION

Figure 1:
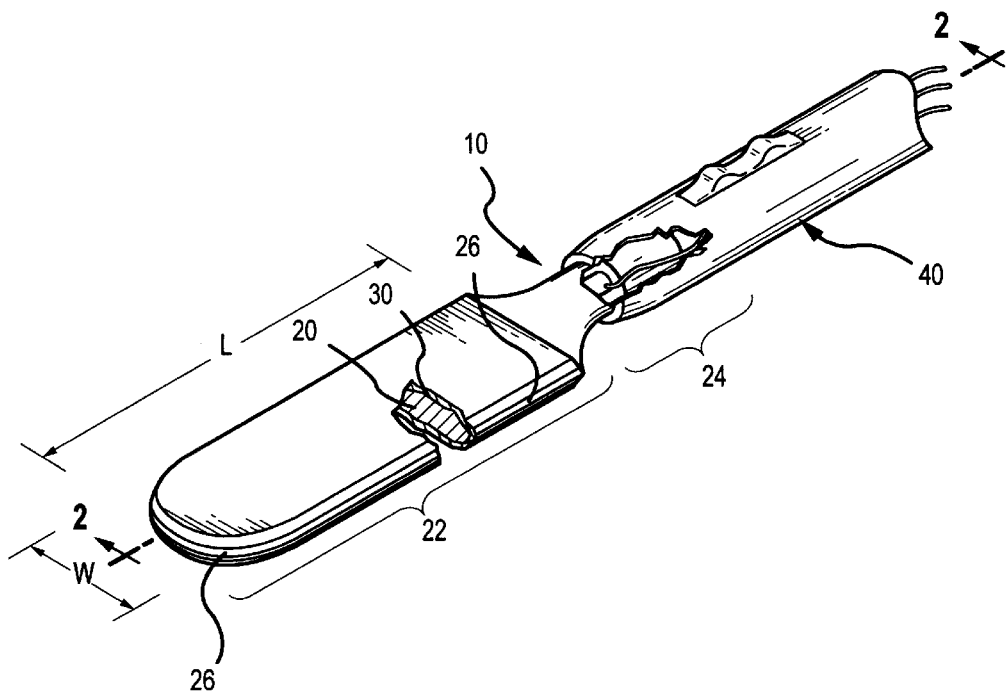
FIG. 1 illustrates a perspective, partial cut-away view of an electrosurgical instrument in one embodiment of the present invention.
Figure 2:
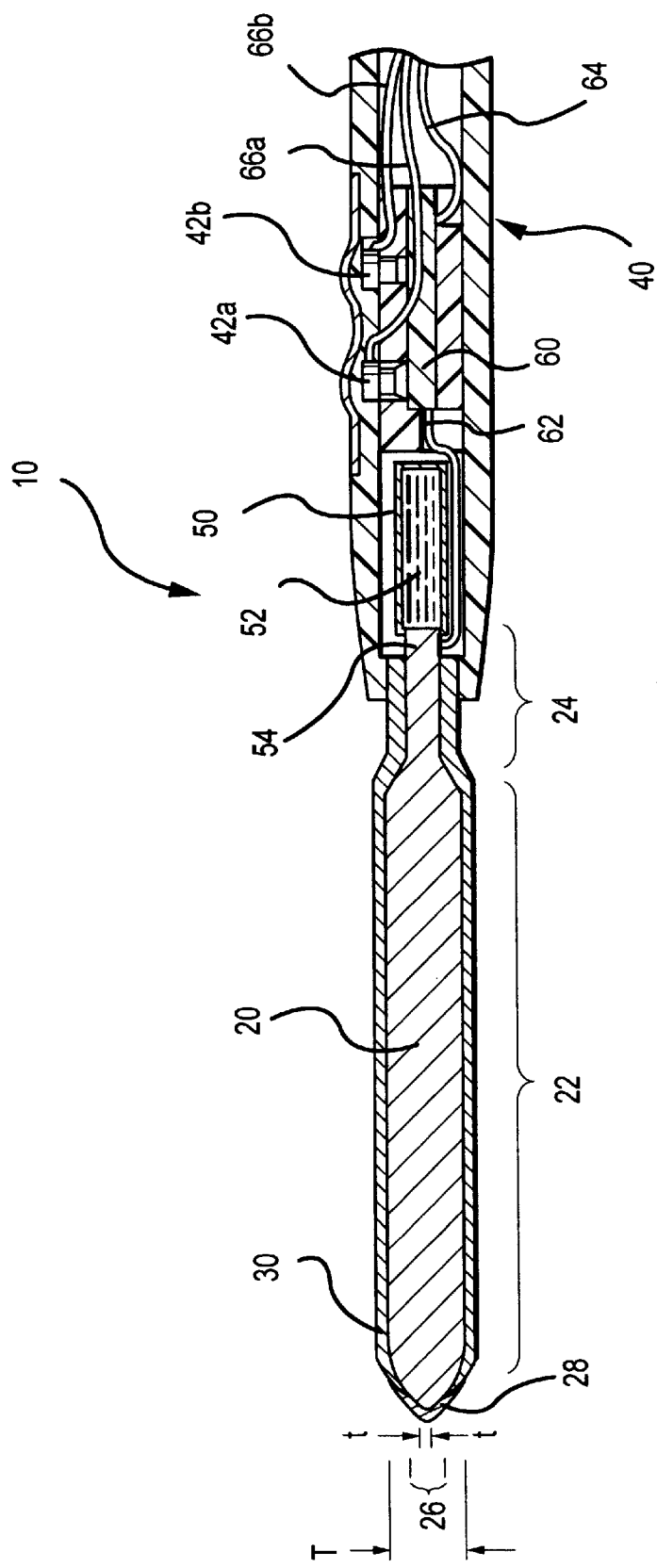
FIG. 2 illustrates a side, cross-sectional view of the electrosurgical instrument embodiment of FIG. 1

FIGS. 1 and 2 illustrate one embodiment of an electrosurgical instrument having a blade-like, pencil configuration. As will be appreciated, the present invention may also be readily embodied in other instrument configurations, including for example, ball electrodes and forceps.

As illustrated in FIGS. 1 and 2, the electrosurgical instrument 10 includes a main body 20 having an outer, insulating layer 30. The main body 20 includes a flattened, forwardly-extending blade portion 22 and a rearwardly-extending cylindrical shaft portion 24. The blade portion 22 is tapered laterally outward (i.e. in cross-sectional thickness) to a relatively thin outer peripheral edge about at least a rounded, forward end to define peripheral edge portion 26. In the illustrated embodiment, peripheral edge portion 26 is not covered by insulating layer 30. Preferably, peripheral edge portion 26 has outer extreme edge thickness t of about 0.001 inches or less. Further, the maximum thickness of edge portion 26 is preferably no more than about 1/10 of the maximum thickness T of main body 20.

The main body 20 should comprise a metal having a relatively high thermal conductivity (e.g. at least about 0.35 W/cm° K when measured at 300° K). In particular, main body 20 may advantageously comprise a metal selected from the group comprising: copper, silver, gold, aluminum, tungsten, tantalum, columbium and molybdenum. Alloys of such metals (e.g., at least about 50% by weight), may also be employed. The use of such metals in the main body 20 allows for not only effective delivery of an electrosurgical signal therethrough for transmission via peripheral edge portion 26 to a tissue site, but additionally facilitates the removal of heat rearwardly away from peripheral edge portion 26 during operation. Such heat removal reduces undesired heat transfer from the electrosurgical instrument 10 to a tissue site during use. In the event copper is utilized for main body 20 in the FIG. 1 embodiment, a biocompatible plating 28 (e.g. nickel, gold, silver, chrome or titanium) may be selectively applied to peripheral edge 26.

The insulating layer 30 should provide both thermal and electrical insulation capabilities so as to reduce the discharge of thermal and electrical energy, respectively, from electrosurgical instrument 10 during use. For example, the outer insulating layer 30 should most preferably comprise a material having a thermal conductivity of about 0.009 W/cm-° K or less when measured at about 300° K. Further, the insulation layer should exhibit a dielectric withstand voltage of at least about 50 volts, and more preferably at least about 150 volts. By way of example, layer 30 may comprise a silicon-based, polymeric material (e.g., at least about 10% silicon by weight) and/or a ceramic-based material.

While several production techniques may be utilized to apply the insulating layer 30 to the main body 20, one approach that has been found particularly effective is to first treat the metal surface of main body 20 with an appropriate primer, such as a silane, before applying the insulating layer. Such priming further enhances the ability of silicon-based polymers to adhere to the outer surface of the main body 20. Such adherence is particularly advantageous since during use the main body 20 and insulating layer 30 may be bent or otherwise configured by medical personnel in the course of an electrosurgical procedure. By way of example, when a silicon-based polymer such as RTV 160, offered by General Electric Company, is employed, a suitable primer would be Z6020, offered by General Electric Company. Alternatively, when MED4940, offered by NuSil Technology, is employed as a silicon-based polymer, a suitable primer is CF2-135, offered by NuSil Technology.

Following priming, the insulating layer 30 may be selectively applied to main body portion 20 via a coating process so as to substantially cover main body 20. Preferably, the peripheral edge portion 26 is selectively left uncovered by insulative coating 30. Selective coating may be accomplished by several techniques, including, for example, the use of an injection molding process, by a masking/coating/mask removal process, or by coating the entirety of the main body 20 with insulating layer 30 and selectively removing the insulative coating from the peripheral edge portion 26.

As best shown in FIG. 2, the shaft portion 24 of the main body 20 is supportably fitted into a forward end of an elongated holder assembly 40 that is adapted for hand-held use and manipulation by medical personnel. Such supportive interface may be either permanent (e.g. wherein the entire electrosurgical instrument 10 is disposed of after use), or the interface may be designed for selective insertion/removal of the main body 20 into/from welder assembly 40 (e.g. wherein the holder assembly 40 may be reused). In the embodiment of FIGS. 1 and 2, the holder assembly 40 houses a vessel 50 containing a phase change material 52. The vessel 50 is provided with a thermally conductive interface such as a thermally conductive pad 54, which may butt against the end of the shaft portion 24 of main body 20, as shown in FIG. 2, or which may partially or totally surround the shaft portion, at one end for direct contact and thermal interface with the end of shaft portion 24 of the main body 20.

The phase change material 52 may be selected to provide an effective heat sink for removal of thermal energy from main body 20. More particularly, the phase change material 52 may preferably maintain main body 20 at an average temperature of about 500° C. or less, more preferably at about 200° C. or less, and most preferably at about 100° C. or less. For such purposes, the phase change material may be provided to change from a first phase to a second phase (e.g., solid to liquid) at a predetermined temperature of at least about 40° C. Further, for the arrangement of FIG. 1, it has been found that when a 100 W signal is applied to main body 20, phase change material 52 should be capable of removing at least about 8 W of thermal energy.

By way of example, phase change material 52 may comprise a material that is an organic substance (e.g., fatty acids such as stearic acid, hydrocarbons such as paraffins) or an inorganic substance (e.g., water, and water compounds containing sodium, such as sodium silicate (2-)-5 water, sodium sulfate-10-water). Phase change material 52 may undergo phase changes of melting, vaporization, or sublimation, although melting and vaporization are preferred. Most preferably, the phase change temperature is greater than about 40° C. and less than about 85° C. While FIGS. 1–2 illustrate that phase change material 52 is contained within vessel 50, phase change material 52 may be alternatively disposed within and circulated through a sealed passageway within holder assembly 40.

The holder assembly 40 may further comprise one or more switch buttons 42a, 42b for the selective application of a predetermined electrosurgical signal to the main body portion 20. More particularly, switch button 42a may be depressed to electrically contact a metal plate 60, wherein an electrosurgical signal for tissue cutting may be provided to plate 60 and in turn to main body 20 via line 62. Similarly, switch button 42b may be depressed to electrically contact metal plate 60, wherein an electrosurgical signal for tissue coagulation may be provided to plate 60 and in turn main body 20 via line 62. Source signal line 64 as well as source signal return lines 66a and 66b may all be provided for receiving/returning signals to an RF electrosurgical source generator in a conventional fashion.

In one arrangement, electrosurgical instrument 10 comprises a blade portion 22 having a thickness T of about 0.040 inches (see FIG. 3), a width W of about 0.140 inches and length L of about 1 inch. In such arrangement, the main body 20 comprises copper (e.g., about 98% by weight) and insulating layer 30 has a thickness of about 0.010 inches and comprises a polymeric, silicon-based material. Further, a phase change material comprises about 2 grams of stearic acid. This arrangement has been found particularly effective to yield reduced smoke generation and tissue charring.

Figure 3:
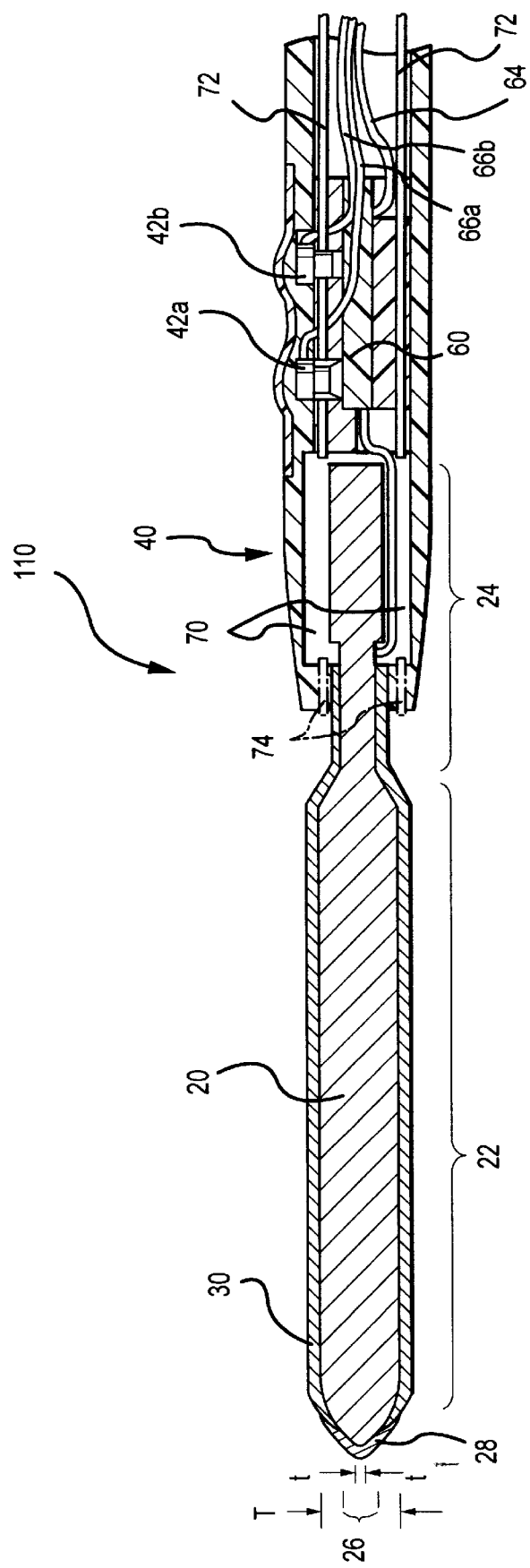
FIG. 3 illustrates a side, cross-sectional view of another electrosurgical instrument embodiment of the present invention.

FIG. 3 illustrates an alternate embodiment of an electrosurgical instrument 110 and is largely of the same construction as electrosurgical instrument 10 illustrated in FIGS. 1 and 2. As opposed to utilizing a phase change material 52 for the removal of thermal energy from main body 20, however, the embodiment illustrated in FIG. 3 utilizes a cooling gas stream that is circulated through an internal channel 70 of holder assembly 40 to remove thermal energy from shaft portion 24 of main body 20. As illustrated, channel 70 may be interconnected to a gas source via tubing lines 72 for circulation/cooling. In a modification of the embodiment shown in FIG. 3, channel 70 may be modified to pass directly on through conduits 74 at the forward extreme of holder assembly 70, and through an annuler outlet 76 positioned immediately about the main body 20, wherein the cooling gas passing therethrough contacts the peripheral edge portion 26 for heat removal purposes. In yet other arrangements, the heat sink employed may utilize a liquid stream, a combination liquid/gas stream, gas and liquid streams that are separate (e.g., a heat pipe), and a thermal mass (e.g., a copper block).

Figure 4:
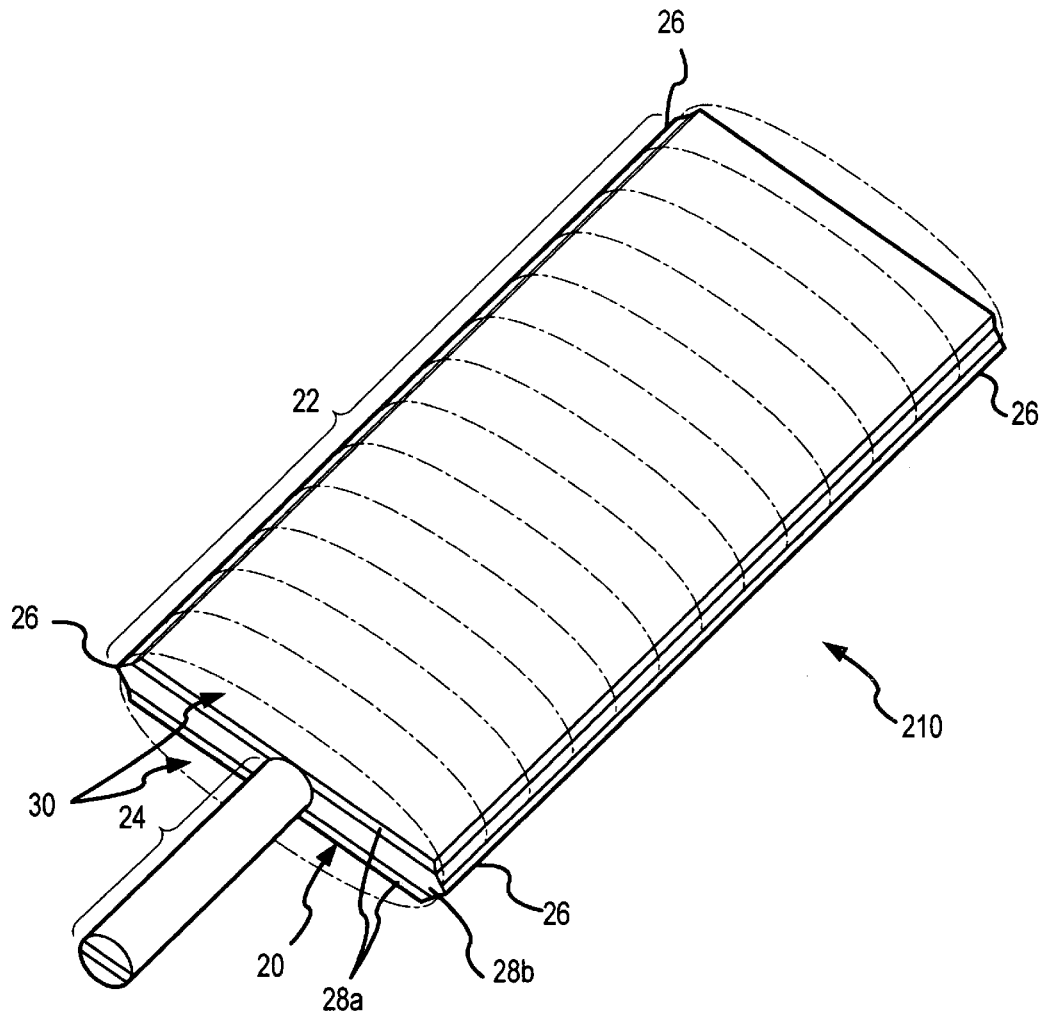
FIG. 4 illustrates a perspective view of yet another electrosurgical instrument embodiment of the present invention.
Figure 5:
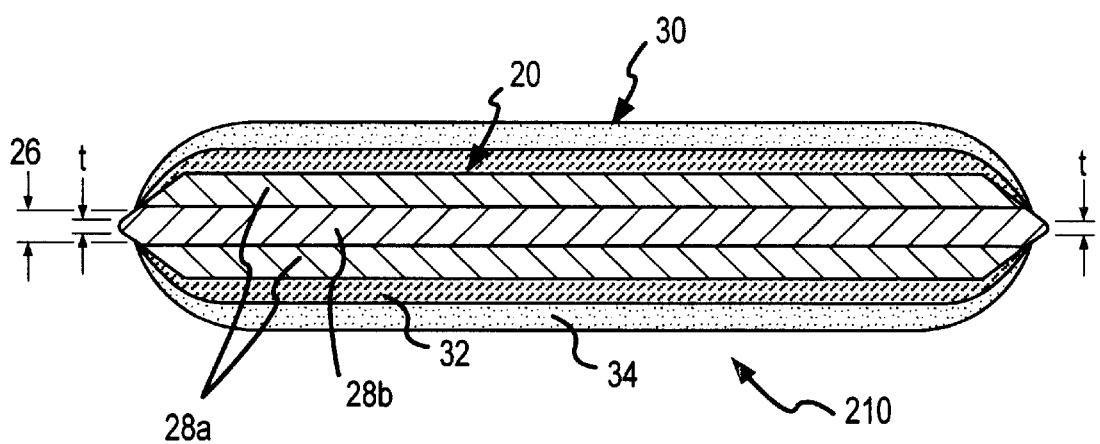
FIG. 5 illustrates a cross-sectional view of a blade portion of the electrosurgical instrument embodiment of FIG. 4.

FIGS. 4 and 5 illustrate a further alternate embodiment of an electrosurgical instrument 210. As shown, electrosurgical instrument 210 includes a main body 20 defined by a laminate structure consisting of top and bottom layers 28a and an intermediate layer 28b sandwiched therebetween. Electrosurgical instrument 210 further includes an insulating layer 30 defined by inner top/bottom layers 32 and outer top/bottom layers 34. As illustrated, a peripheral edge portion 26 of the intermediate layer 28b is exposed (i.e., not covered by insulating layer 30). Preferably, such peripheral edge portion 26 has an outer, extreme edge thickness t of about 0.001 inches or less. Further, in the illustrated embodiment, the peripheral edge portion 26 is approximately centered about a center plane of the intermediate layer 28b. Such center plane may further coincide with a center plane of a blade portion 22 of the electrosurgical instrument 210.

The main body 20 preferably comprises metals which have a relatively high thermal conductivity (e.g., at least about 0.35 W/cm° K when measured at 300° K). For example, top and bottom layers 28a may preferably comprise one or more metal selected from a group consisting of gold, silver, aluminum and copper. Such materials have thermal conductivities of at least about 2 W/cm° K when measured at 300° K. Further, intermediate layer 28b of the main body 20 preferably comprises a metal having a melting point of at least about 2600° F. In particular, intermediate layer 28b may comprise one or more materials from a group consisting of tungsten, tantalum, columbium and molybdenum. The intermediate layer 28b and the top and bottom layers 28a may preferably each have a thickness of between about 0.001 and 0.25 inches.

As noted, insulating layer 30 may be defined by inner layers 32 and outer layers 34. By way of example, the top and bottom inner layer 32 may comprise a ceramic material and may preferably each have a thickness of between about 0.001 and 0.20 inches. Top and bottom outer layers 34 may comprise a silicon polymeric material and may preferably each have a thickness of between about 0.001 and 0.020 inches. The insulating layer 30 may be fabricated by first dipping the main body 20 into a green (i.e., uncured) ceramic composition. The dipped main body 20 is then allowed to air dry (e.g., wherein solution carriers in the ceramic composition are allowed to evaporate). After drying, the ceramic material is removed from the main body 20 to expose peripheral edge portion 26. The main body 20 may then be heated to completely cure the ceramic material in a manner as described above. Thereafter, a silicon polymeric coating is applied over the ceramic material. If needed, a surface conditioning agent (e.g., a silane) may be applied before such coating. Then, the silicon polymeric coating may be removed from peripheral edge portion 26.

In one arrangement, electrosurgical instrument 210 may include a main body 20 with an intermediate layer 28b that comprises an alloy comprising at least about 95% molybdenum by weight. In such arrangement, top and bottom layers 28a may comprise a copper alloy containing at least about 95% copper by weight. The intermediate layer 28b and top and bottom layers 28a may each be defined at a thickness of about 0.010 inches. Each of the top/bottom insulating layers 32 and top/bottom insulating layers 34 may have a thickness of about 0.005 to 0.015 inches. While not shown, the shaft portion 24 in the described arrangement may interface with a heat sink (e.g., a thermal mass disposed within a handle portion).

Numerous additional embodiments and modifications will be apparent to those skilled in the art and are encompassed by the present invention as defined by the claims which follow.

What is claimed is:

1. An electrosurgical instrument for conveying an electrosurgical signal to tissue to achieve a predetermined electrosurgical effect, comprising:

a metal body having a thermal conductivity of at least about 0.35 W/cm° K when measured at about 300° K and having a peripheral edge portion defined by a material with a melting point of at least about 2600° F.; and an outer insulating layer positioned over at least a portion of said metal body.

2. An electrosurgical instrument as recited in claim 1, wherein said peripheral edge portion is exposed, and wherein an electrosurgical signal is conveyable to tissue substantially entirely through said peripheral edge portion.

3. An electrosurgical instrument as recited in claim 1, wherein said metal body comprises:
   a first metal layer defining said peripheral edge portion; and
   at least one second metal layer adjacent to said first metal layer, wherein said first metal layer and said at least one second metal layer comprise different materials.

4. An electrosurgical instrument as recited in claim 3, wherein said first metal layer comprises a first material selected from a group consisting of tungsten, tantalum, columbium and molybdenum.

5. An electrosurgical instrument as recited in claim 4, wherein said first material comprises at least about 50% by weight of said first metal layer.

6. An electrosurgical instrument as recited in claim 5, wherein said first material comprises at least about 90% by weight of said first metal layer.

7. An electrosurgical instrument as recited in claim 3, wherein said at least one second metal layer has a thermal conductivity of at least about 2 W/cm° K when measured at about 300° K.

8. An electrosurgical instrument as recited in claim 7, wherein said at least one second metal layer comprises a second material selected from a group consisting of gold, copper, aluminum and silver.

9. An electrosurgical instrument as recited in claim 8, wherein said first metal layer comprises a first material selected from a group consisting of tungsten, tantalum, columbium and molybdenum.

10. An electrosurgical instrument as recited in claim 8, wherein said second material comprises at least about 50% by weight of said at least one second metal layer.

11. An electrosurgical instrument as recited in claim 10, wherein said second material comprises at least about 90% by weight of said at least one second metal layer.

12. An electrosurgical instrument as recited in claim 7, wherein said first metal layer comprises a first material selected from a group consisting of tungsten, tantalum, columbium and molybdenum.

13. An electrosurgical instrument as recited in claim 3, further comprising:
   at least two second metal layers with said first metal layer positioned therebetween.

14. An electrosurgical instrument as recited in claim 13, wherein said first metal layer is of a thickness of between about 0.001 and 0.25 inches, and wherein each of said two second metal layers are of a thickness of between about 0.001 and 0.25 inches.

15. An electrosurgical instrument as recited in claim 13, wherein said at least two second metal layers each have a thermal conductivity of at least about 2 W/cm° K when measured at about 300° K.

16. An electrosurgical instrument as recited in claim 15, wherein said first metal layer comprises a first material selected from a group consisting of tungsten, tantalum, columbium and molybdenum.

17. An electrosurgical instrument as recited in claim 16, wherein said at least two second metal layers each comprise a second material selected from a group consisting of gold, copper, aluminum and silver.

18. An electrosurgical instrument as recited in claim 1, wherein said outer insulating layer has a maximum thermal conductance of about 1.2 W/cm° K when measured at about 300° K.

19. An electrosurgical instrument as recited in claim 18, wherein said outer insulating layer comprises:
   an inner layer; and
   an outer layer, wherein said first inner layer and said second outer layer comprise different materials.

20. An electrosurgical instrument as recited in claim 19, wherein said inner layer comprises a ceramic material, and wherein said outer layer comprises a polymeric material.

21. An electrosurgical instrument as recited in claim 18, wherein said metal body comprises:
   a first metal layer defining said peripheral edge portion; and
   at least one second metal layer adjacent to said first metal layer, wherein said first metal layer and said at least one second metal layer comprise different materials.

22. An electrosurgical instrument as recited in claim 21, wherein said at least one second metal layer has a thermal conductivity of at least about 2 W/cm° K when measured at about 300° K.

23. An electrosurgical instrument as recited in claim 22, wherein said first metal layer comprises a first material selected from a group consisting of tungsten, tantalum, columbium and molybdenum.

24. An electrosurgical instrument as recited in claim 23, wherein said at least one second metal layer comprises a second material selected from a group consisting of gold, copper, aluminum and silver.

25. An electrosurgical instrument for conveying an electrosurgical signal to tissue to achieve a predetermined electrosurgical effect, comprising:
   a metal body having a peripheral edge portion defined by a material with a melting point of at least about 2600° F., wherein an outer extreme of said peripheral edge portion is of a thickness of about 0.001 inches or less; and,
   an outer insulating layer positioned over at least a portion of said metal body, wherein said peripheral edge portion is left exposed.

26. An electrosurgical instrument as recited in claim 25, wherein said metal body comprises:
   a first metal layer defining said peripheral edge portion; and,
   at least one second metal layer adjacent to said first metal layer, wherein said first metal layer and said at least one second metal layer comprise different materials.

27. An electrosurgical instrument as recited in claim 26, wherein said first metal layer has a thermal conductivity of at least about 0.35 W/cm° K when measured at 300° K, and wherein said second metal layer has a thermal conductivity of a least of about 2 W/cm° K when measured at about 300° K.

28. An electrosurgical instrument as recited in claim 27, wherein said first metal layer comprises a metal selected from a group consisting of tungsten, tantalum, columbium and molybdenum, and wherein said at least one second metal layer comprises a material selected from a group consisting of gold, copper, aluminum and silver.

29. An electrosurgical instrument as recited in claim 27, wherein said outer insulating layer has a maximum thermal conductance of about 1.2 W/cm° K when measured at about 300° K.

30. An electrosurgical instrument as recited in claim 29, wherein said outer insulating layer comprises:
   in inner layer comprising a ceramic material; and,
   an outer layer comprising a polymeric material.

31. An electrosurgical instrument as recited in claim 30, wherein said first metal layer comprises a metal selected from a group consisting of tungsten, tantalum, columbium and molybdenum, and wherein said at least one second metal layer comprises a material selected from a group consisting of gold, copper, aluminum and silver.

32. An electrosurgical instrument as recited in claim 25, wherein said outer insulating layer comprises:

in inner layer comprising a ceramic material; and, an outer layer comprising a polymeric material.

33. An electrosurgical instrument for conveying an electrosurgical signal to tissue to achieve a predetermined electrosurgical effect, comprising:

a metal body having a thermal conductivity of at least about 0.35 W/cm° K when measured at about 300° K and having a peripheral edge portion defined by a material with a melting point of at least about 2600° F., wherein said metal body comprises:

a first metal layer defining said peripheral edge portion; and at least one second metal layer adjacent to said first metal layer, wherein said first metal layer and said at least one second metal layer comprise different materials, and wherein said at least one second metal layer has a thermal conductivity of at least about 2 W/cm° K when measured at about 300° K; and an outer insulating layer positioned over at least a portion of said metal body, wherein said outer insulating layer has a maximum thermal conductance of about 1.2 W/cm²-° K when measured at about 300° K.

34. An electrosurgical instrument as recited in claim 33, wherein said first metal layer comprises a metal selected from a group consisting of tungsten, tantalum, columbium and molybdenum, and wherein said at least one second metal layer comprises a material selected from a group consisting of gold, copper, aluminum and silver.

35. An electrosurgical instrument as recited in claim 33, further comprising:

at least two second metal layers with said first metal layer positioned therebetween.

36. An electrosurgical instrument as recited in claim 35, wherein said first metal layer comprises a metal selected from a group consisting of tungsten, tantalum, columbium and molybdenum, and wherein said at least two second metal layers each comprise a material selected from a group consisting of gold, copper, aluminum and silver.

37. An electrosurgical instrument as recited in claim 33, wherein said outer insulating layer comprises:

an inner layer; and an outer layer, wherein said first inner layer and said second outer layer comprise different materials.

38. An electrosurgical instrument as recited in claim 37, wherein said inner layer comprises a ceramic material, and wherein said outer layer comprises a polymeric material.

* * * * *